United States Patent [19]

Smith

[11] Patent Number: 4,670,227

[45] Date of Patent: Jun. 2, 1987

[54] APPARATUS AND METHOD FOR HANDLING OF INFECTIOUS WASTE MATERIAL

[75] Inventor: William B. Smith, Bloomington, Ill.

[73] Assignee: Bio-Environmental Systems, Inc., Champaign, Ill.

[21] Appl. No.: 640,000

[22] Filed: Aug. 10, 1984

[51] Int. Cl.$^4$ .............................................. A61L 3/00
[52] U.S. Cl. ..................................... 422/297; 53/512; 280/47.35; 414/420
[58] Field of Search .................................. 422/26–27, 422/294, 297, 300, 119; 53/511, 512, 527; 280/47.26, 47.34, 47.35; 414/420

[56] References Cited

U.S. PATENT DOCUMENTS

| | | | |
|---|---|---|---|
| 1,409,286 | 3/1922 | Diner | 422/297 X |
| 2,958,540 | 11/1960 | Wheeler | 280/47.26 X |
| 3,179,332 | 4/1965 | Brighton et al. | 280/47.26 X |
| 3,241,750 | 3/1966 | Brighton | 280/47.26 X |
| 3,262,713 | 7/1966 | Crawford | 280/47.26 |
| 3,738,516 | 6/1973 | Wells | 280/47.26 X |
| 3,837,512 | 9/1974 | Brown | 414/420 X |
| 3,923,174 | 12/1975 | Straiger | 414/420 |
| 3,994,684 | 11/1976 | Tomasulo | 422/26 X |
| 4,447,399 | 5/1984 | Runnetts et al. | 422/109 X |
| 4,459,936 | 7/1984 | Karle | 422/26 X |
| 4,552,720 | 11/1985 | Baker et al. | 422/26 |

FOREIGN PATENT DOCUMENTS

0912170 3/1982 U.S.S.R. ............................... 422/300

Primary Examiner—Barry S. Richman
Assistant Examiner—William R. Johnson
Attorney, Agent, or Firm—Neal J. Mosely

[57] ABSTRACT

Apparatus for safe handling of biologically infectious waste materials comprises providing paper or plastic bags to receive infectious waste material, an open collection cart for receiving said bags, an enclosed transport cart for receiving, enclosing, and transporting the collection cart, placing the collection cart inside the transport cart, depositing the plastic bags into the collection cart while disposed within the transport cart, transferring the collection cart and bags of infectious waste into a sterilizing chamber, sterilizing the infectious waste material by steam heat, exposing fluids produced during the sterilization process to steam heat for a time sufficient to sterilize the same by allowing the fluids to slowly drain from said bags to a fluid receiver at the bottom of the collection cart and then to a second fluid receiver at the bottom of the sterilizing chamber and into a conventional drainage system, transferring the collection cart to a dumping and compacting apparatus, dumping and compacting the material, and finally disposing of the compacted sterilized waste material by conventional methods such as burial or incineration.

29 Claims, 13 Drawing Figures fig. 1 fig.4 fig.5 fig.3 fig.7 fig.6 fig.8

APPARATUS AND METHOD FOR HANDLING OF INFECTIOUS WASTE MATERIAL

BACKGROUND OF THE INVENTION

1. Field of the Invention

This invention relates to waste disposal systems, and more particularly to a method and apparatus for safe handling of biologically hazardous infectious waste materials.

2. Brief Description of the Prior Art

The handling, transporting and disposal of infectious waste materials in hospitals, bio-medical facilities, and research laboratories presents a substantial hazard for the accidental dispersal of pathogenic agents into the environment. Waste materials collected from such facilities may include such things as human and animal body parts, tissues, soiled bandages, medications, chemicals, syringes, scalpels, needles, etc.

Some prior art systems for the management and disposal of biologically hazardous infectious waste materials consists of collecting the waste in a plastic bag, storing it in a utility room and periodically transporting in an open cart it to an incinerator or autoclave for sterilization and/or disposal. On some occasions, the hazardous waste materials may inadvertently be collected and transported to a land fill for burial without first even being decontaminated.

Steam sterilization is a primary method used to decontaminate infectious waste materials in the aforementioned facilities. The steam sterilization process employs high temperatures (in excess of 250° F.) to kill pathogenic microorganisms. Heat may be by direct steam contact, or by conduction.

The prior art in general does not suggest the present apparatus and method of handling biologically infectious waste materials to prevent contamination from the handling of such waste materials.

SUMMARY OF THE INVENTION

It is therefore one object of the present invention to provide a method and apparatus for handling biologically infectious waste materials to prevent contamination from the handling of the waste materials.

Another object of this invention is to provide a method and apparatus which will guard the patients and staff of hospitals, bio-medical facilities, and research laboratories against potential cross contamination of microbial transmission which may be generated as a result of handling plastic bags containing biologically infectious waste material.

Another object of this invention is to provide a method and apparatus to provide sanitary protection in the waste storage and collection areas of hospitals, bio-medical facilities, research laboratories and the like.

Other objects of the invention will become apparent from time to time throughout the specification and claims as hereinafter related.

The above noted objects and other objects of the invention are accomplished by the present apparatus and method of handling biologically infectious waste materials comprising placing a collection cart of generally open construction into an enclosable transport cart, collecting the infectious waste material in paper or plastic bags, depositing the bags of material into the collection cart while contained in the transport cart, transferring the collection cart and bags of infectious waste material into a sterilizing chamber, sterilizing the infectious waste material and fluids, allowing the sterilized fluids to enter a conventional drainage system and finally compacting the sterilized waste for disposal by conventional methods such as burial or incineration.

DESCRIPTION OF THE PREFERRED EMBODIMENT

Figure 1:
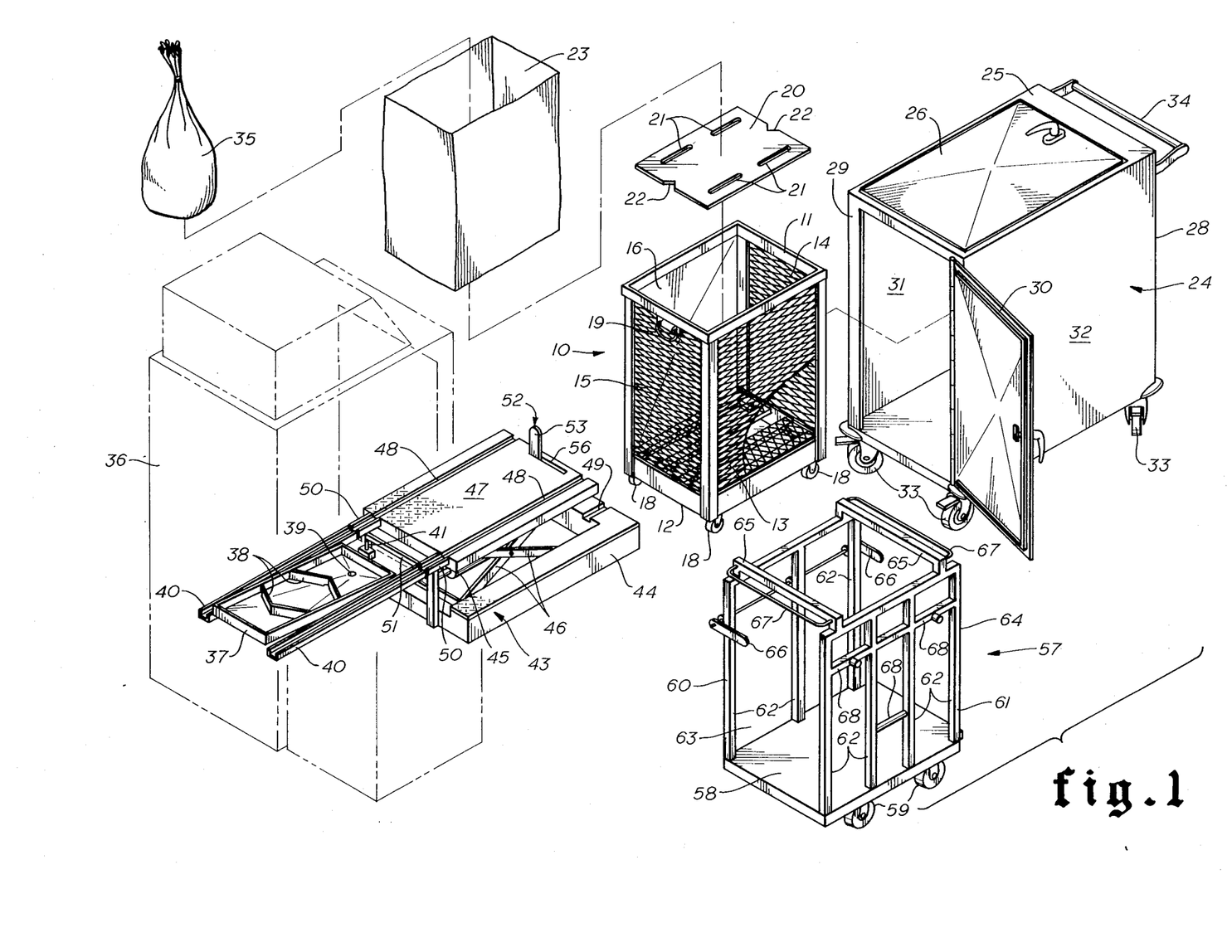
FIG. 1 is an exploded isometric view of the apparatus for handling of infectious waste in accordance with the present invention.
Figure 2:
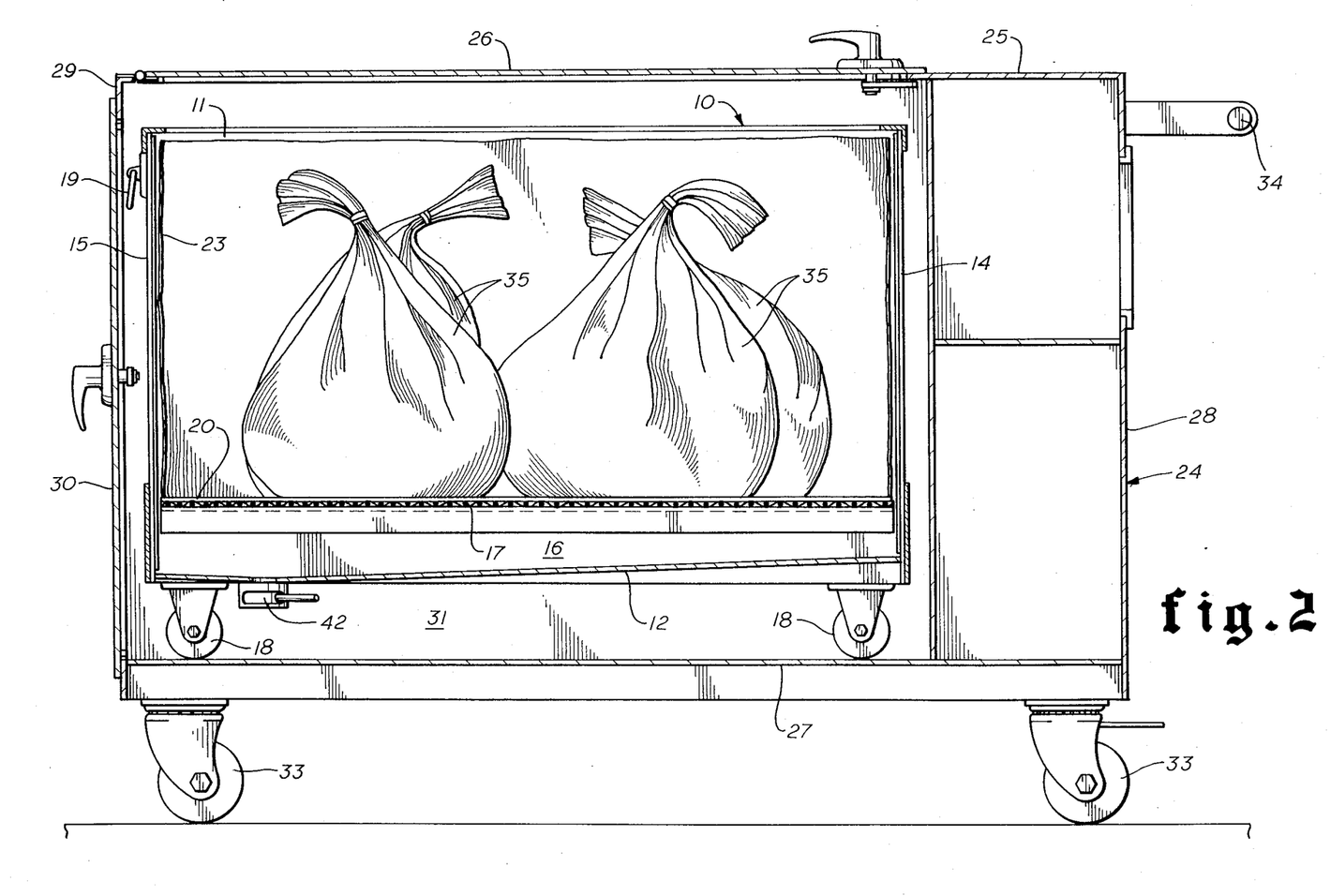
FIG. 2 is a view in side elevation in cross section of the collection cart contained within the transport cart.
Figure 3:
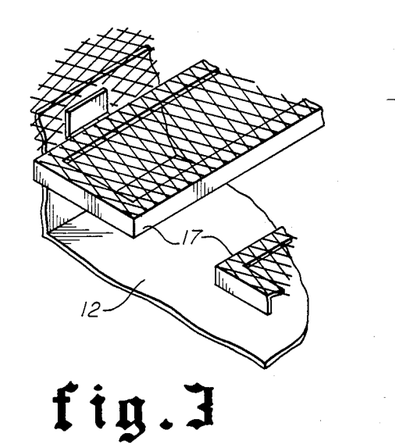
FIG. 3 is a partial isometric view of a portion of the interior of the collection cart showing a raised platform member.

Referring to the drawings by numerals of reference, and particularly to FIGS. 1-3, there is shown apparatus used for the handling of biologically infectious waste material. A collection cart 10 is provided which has an open top 11, an enclosed bottom 12, three sides formed of wire mesh 13, 14, and 15, and one side panel 16 enclosed with a sheet of stainless steel to protect the operator during handling operations.

A pair of hinged wire mesh panels 17 form a raised platform slightly above the bottom 12 of the cart 10 to facilitate air removal, steam circulation, and drainage within the cart. The cart 10 is of stainless steel construction or other material suitable to withstand the stresses of steam sterilization. Casters 18 are provided on the bottom and a handle 19 on at least one side of the cart for transporting the cart. The bottom 12 of the cart 10 defines a downwardly and rearwardly sloping drain pan.

A disposable flat corrugated cardboard insert 20, having longitudinal openings or slots 21 therethrough and notches 22 disposed at each end thereof, is inserted into the open end 11 of the cart 10 to rest on the wire mesh panels 17. The slots 21 and notches 22 also facilitate air removal, steam circulation, and fluid drainage within the cart 10. Alternatively, the tray 20 may be provided with four opposed, upwardly extended sides having die-cut hand holes to form a tray-like unit to facilitate manual removal from the cart 10. A heavy weight paper liner 23, such as 80 pound stock, having four sides and an open top and bottom end is placed into the cart 10 against the sides thereof to form a temporary disposable interior lining for the cart 10.

The collection cart 10 thus assembled is received inside of a transport cart 24. The transport cart 24 has a top panel 25 provided with a lockable hinged door 26, an enclosed bottom 27, a back side panel 28, a front end panel 29 provided with a lockable hinged door 30, and two enclosed sides panels 31 and 32. Casters 33 are provided on the bottom and a handle 34 on the back end panel 28 for transporting the cart 24. The front two casters may be lockable to prevent the cart 24 from rolling. The collection cart 10 is placed into the transport cart 24 through the front hinged door 26 with its open top 11 directly beneath the top hinged door 26.

The transport cart 24 containing the collection cart 10 is then wheeled to a suitable location to receive infectious waste material which is collected in paper or plastic bags 35. A typical bag is composed of high density polyethylene material. Alternatively, another type of bag may be used which is constructed of low density polyethylene material which will partially melt upon reaching temperatures in excess of 180° F. to leave openings in the bag permitting rapid air escape and efficient steam penetration. The bags 35 are placed into the collection cart 10 through the top hinged door 26 of the transport cart 24 and are stacked on the cardboard insert 20.

Figure 4:
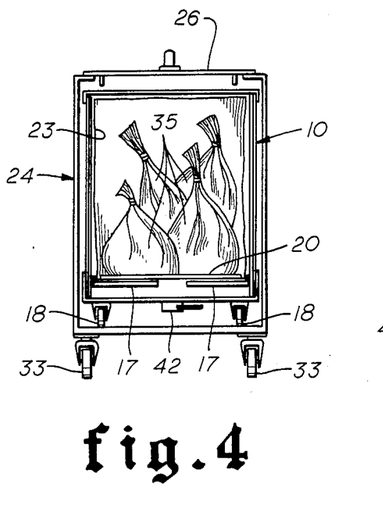
FIG. 4 is a view in end elevation in cross section of the collection cart contained within the transport cart.
Figure 5:
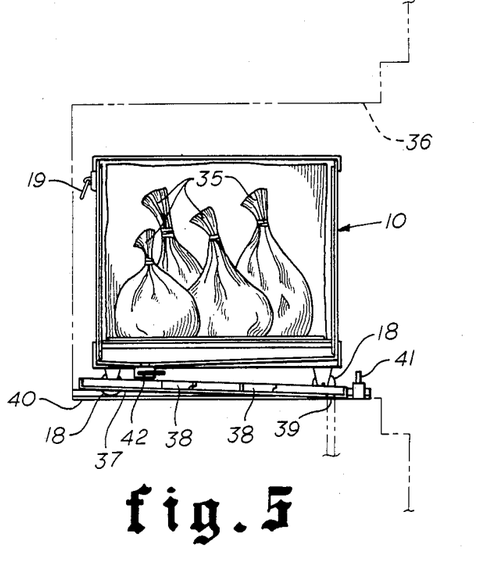
FIG. 5 is a view in side elevation in cross section of the transpoting cart inside of an autoclave showing the drainage means.

Referring now to FIGS. 1, 4 and 5, after the collection cart 10 is filled with the bagged waste material, the transport cart 24 containing the collection cart 10 is wheeled to a steam sterilizer or autoclave 36 for sterilization. The autoclave 36 represented by phantom lines is of conventional construction with certain modifications shown in solid line. The bottom of the autoclave 36 is modified to include a downwardly and forwardly sloping drain pan 37 which is provided with a pair of transverse baffle plates 38. The hole 39 of the drain pan 37 is conventionally connected to the existing autoclave drain system.

A pair of parallel, longitudinally-extending track members 40 disposed on the bottom of the autoclave 36 straddle the drain pan 37 and are aligned to receive the caster wheels 18 of the collection cart 10. An upwardly projecting rod or trigger 41 is located at the bottom of the doorway of the autoclave 36 to open a drain valve 42 on the bottom 12 of the collection cart 10 as it is pushed into the autoclave 36 and close the valve 42 as the cart is removed.

Figure 7:
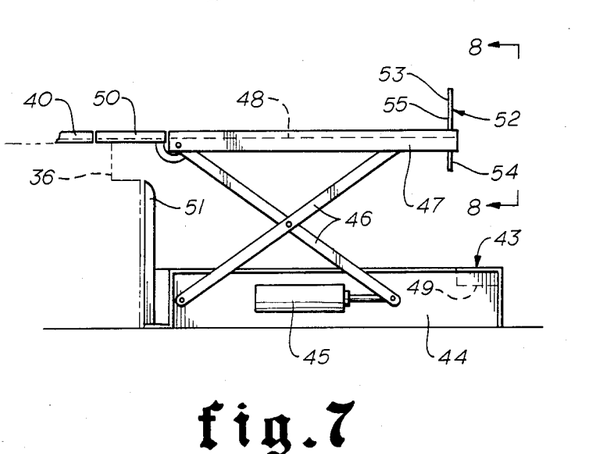
FIG. 7 is a view in elevation in cross section of the lift means.

A hydraulic lift member 43 is disposed directly in front and below the autoclave doorway (FIGS. 1 and 7). The lift 43 comprises a rectangular base 44 of the same height as the bottom of the transport cart 24 and contains a hydraulic cylinder 45 which activates a set of legs 46 in a conventional scissor motion to raise and lower a flat rectangular platform 47. The platform 47 is provided with a set of parallel, longitudinally-extending, recessed tracks 48 which are aligned to receive the caster wheels 18 of the collection cart 10 and in longitudinal alignment with the tracks 40 on the bottom of the autoclave 36. The base 44 is provided with a pair of similarly aligned recessed tracks 49 disposed on its front top surface.

A pair of track extensions 50 in alignment with the aforementioned track members are pivotally connected to the end of the platform 47 nearest the autoclave 36. A horizontally-extending crossbar 51 is provided at the front of the base 44 directly below the extensions 50. When the platform 47 is in the lowermost nested position coplanar with the top surface of the base 44, the extensions 50 strike the crossbar 51 and pivot upwardly 90 degrees to form front stop members to retain the caster wheels 18 of the cart 10 against further forward movement.

A pivotally connected rear stop member 52 (FIGS. 7 and 8) is disposed at the end of the platform 47 farthest from the autoclave 36. The rear stop member 52 comprises a flat rectangular bar 53 having a cammed bottom portion 54 extending below the platform 47 and an upper portion 55 extending above the platform 47 through a slot 56 when the platform is raised. When the pltform 47 is lowered to the nested position the cammed bottom portion 54 of the rear stop 52 contacts the floor, causing the upper portion 55 to pivot downwardly into the slot 56 so that the cart 10 may be removed from the platform.

Figure 8:
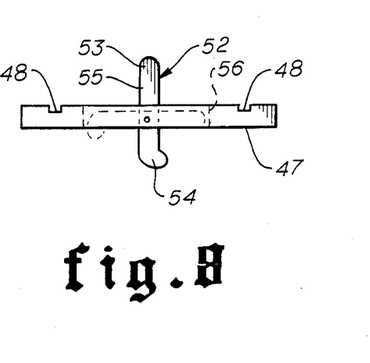
FIG. 8 is a view in end elevation of the platform and rear stop member.
Figures 9, 10, 13:
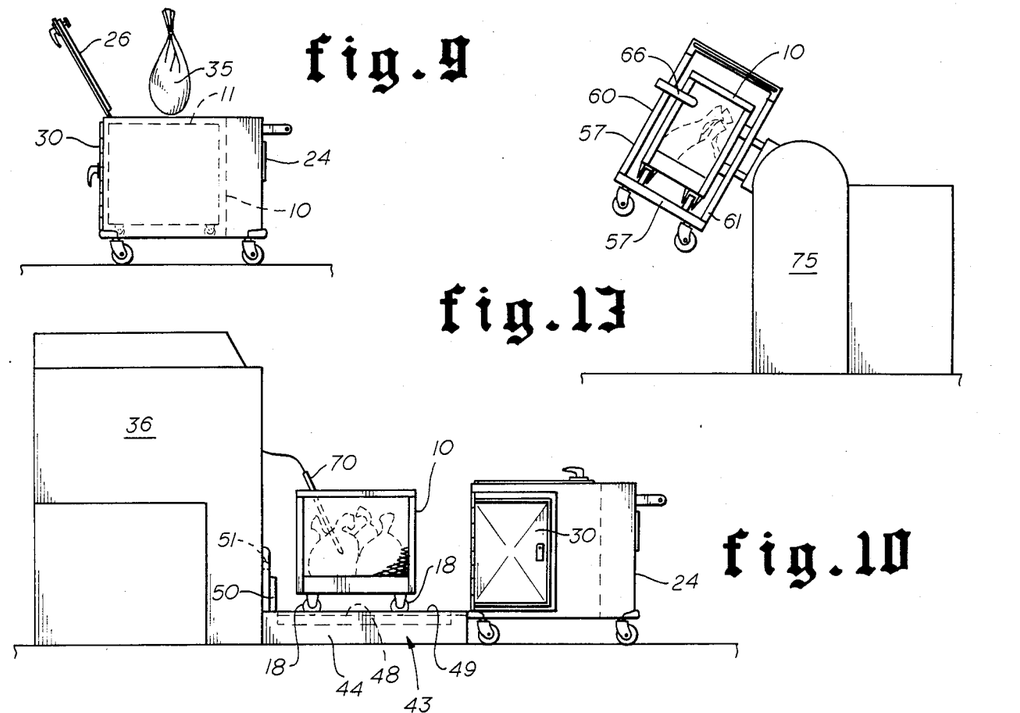
FIGS. 9 through 13 are schematic views illustrating various steps in the method of handling infectious waste material.
Figure 11:
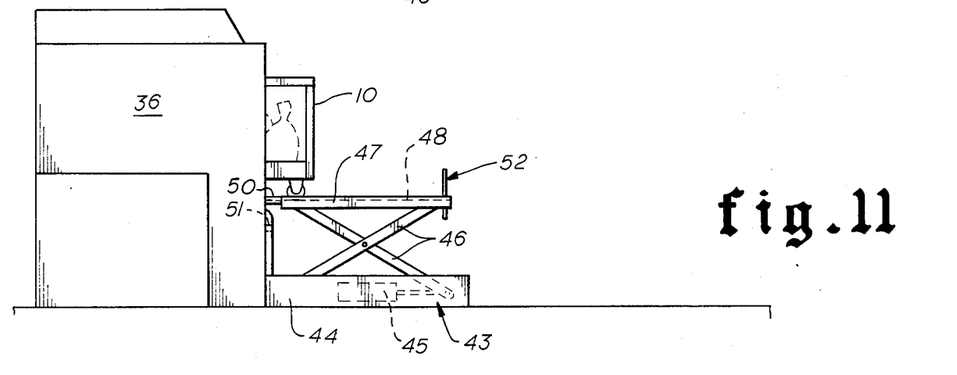
Figure 12:
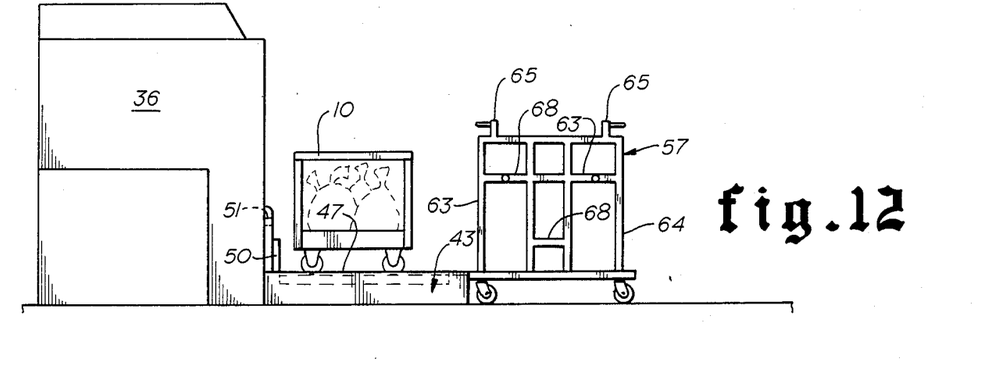

When the platform 47 is raised, the upper portion 55 of the rear stop 52 pivots out of the slot 56 to stand upright at a sufficient height to retain the cart 10 from moving backward. This elevator structure is an optional feature in the waste disposal system which is required only for autoclaves having elevated front openings. In systems having autoclaves with their front doors at ground level, the elevator structure is not required.

After the infectious waste material has been sterilized as described below, a dumping cart 57 (FIG. 1) is placed directly in front of the lift 43 to receive the collection cart 10. The dumping cart 57 has a solid bottom 58 provided with casters 59 for transporting the cart, two opposing sides 60 and 61 formed of tubular upright members 62, and two opposing open ends 63 and 64. A pair of cross bars 65 extend transversely between the top of sides 60 and 61 and are spaced apart a distance less than the length of the open top end 11 of the collection cart 10 to trap the open top end of the cart 10 when the dumping cart 57 is inverted. Pivotal locking arms 66 at each of the open ends 63 and 64 swing and lock in a horizontal position to retain the cart 10 from moving outward through the open ends. Handles 67 disposed at each end of the dumping cart 57 allow the cart to be pulled to the general waste disposal area. The dumping cart 57 is provided with brackets crossmembers 68 on one side which are adapted to receive the existing lifting members of a conventional dumping compactor device.

METHOD AND OPERATION

Referring now to FIGS. 2, 4, and 5 and FIGS. 9 through 13, the method of handling biohazardous infectious waste materials and operation of the apparatus will be explained.

The flat corrugated cardboard insert 20 is inserted into the open end 11 of the collection cart 10 to rest on the wire mesh panels 17, and the heavy weight paper liner 23 is placed into the cart 10 against the sides thereof to form a temporary disposable interior lining for the cart.

The collection cart 10 thus assembled is placed inside of the transport cart 24 through the front hinged door 30 with its open top 11 directly beneath the top hinged door 26, and the transport cart 24 containing the collection cart 10 is then wheeled to a suitable location to receive infectious waste material which is collected in paper or plastic bags 35. The bags 35 are placed into the collection cart 10 through the top hinged door 26 of the transport cart 24 and are stacked on the cardboard insert 20.

After the collection cart 10 is filled with the bagged waste material, the transport cart 24 containing the enclosed collection cart 10 is wheeled to a steam sterilizer or autoclave 36 for sterilization. With the doors of the transport cart closed, the cart may be safely carried onto elevators and wheeled through corridors, etc.

The front door 30 of the transport cart 24 is opened and the cart is positioned directly in front of the base 44 of the hydraulic lift member 43 with the caster wheels 18 of the collection cart 10 in alignment with the tracks 49 of the base 43. The front pair of casters 33 of the transport cart 24 may be locked to prevent the cart from moving. The door of the autoclave 36 is opened and the collection cart 10 is pulled from the transport cart 24 onto the platform 47. When the platform 47 is in the lowermost nested position coplanar with the top surface of the base 44 to receive the cart 10, the track extensions 50 strike the crossbar 51 and pivot upwardly 90° to retain the caster wheels 18 of the cart 10 against further forward movement.

A biological indicator probe 70 containing a thermocouple may then be placed into the pile of collected bags of waste material to monitor the temperature of the material independently of the temperature of the autoclave chamber. Probe 70 is connected to an indicator dial or digital readout outside the autoclave. The wires from the probe may go around the door to the autoclave or through a conventional pressure fitting for passing wires through the wall of a pressure vessel.

The hydraulic cylinder 45 is actuated to activate the legs 46 in a scissor motion to raise the platform 47. As the platform 47 is raised, the rear stop member 52 extends upwardly from the platform to retain the cart 10 from moving backward. As the platform 47 reaches the height of the bottom of the doorway of the autoclave 36, the front track extensions 50 pivot downward to link the tracks 48 of the platform to the tracks 40 disposed within the autoclave 36.

Figure 6:
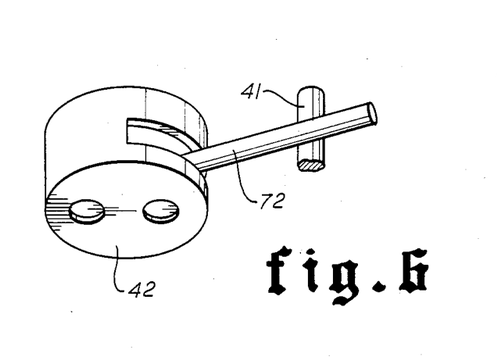
FIG. 6 is an isometric view of the drain valve mechanism of the transport cart.

The collection cart 10 is then pushed from the platform 47 into the autoclave 36. As the cart 10 enters the autoclave 36 the upwardly projecting rod or trigger 41 located at the bottom of the doorway of the autoclave 36 strikes a lever arm 72 extending outwardly from the drain valve 42 disposed at the front of the bottom of the collection cart 10 to open the drain valve as the cart enters the autoclave (FIGS. 5 and 6).

The door of the autoclave 36 is then closed and the cart 10 and the waste material is subjected to steam heat at 15–35 psi and 250° to 280° F. to kill pathogenic organisms. Steam enters from the top, and air being heavier than steam goes out the bottom. The liquids gravitate to the bottom drain pan 12 in the bottom of the collection cart 10 and exit through the open valve 42 into the drain pan 37 of the autoclave 36.

The bottom drain pan 12 of the cart 10 and the drain pan 37 of the autoclave 36 are inclined in opposing relationship and the drain pan 37 of the autoclave is provided with a pair of transverse baffle plates 38 to facilitate maximum time exposure to decontaminate the liquid until it safely enters the existing autoclave drain system. An optional post heating operation consisting of exposing the load to dry heat will melt the syringes and other plastic articles contained in the waste materials.

When the sterilization process is completed, the door of the autoclave 36 is opened, the cart 10 is pulled from the autoclave onto the platform 47. The cart 10 should be handled at this point in time with a grappling hook, gloves, or other suitable means to protect the operator from direct contact with the hot cart. As the cart 10 is removed from the autoclave 36 the upwardly projecting rod or trigger 41 located at the bottom of the doorway of the autoclave again strikes the lever arm 72 of the drain valve 42 to close the valve as the cart exits the autoclave. The back stop member 52 prevents the cart from further backward movement.

The hydraulic cylinder 45 is once again actuated to activate the legs 46 in a scissor motion to lower the platform 47. As the platform 47 is lowered to the nested position coplanar with the stop surface of the base 44, the cammed bottom portion 54 of the rear stop contacts the floor, causing the upper portion 55 to pivot downwardly into the slot 56 so that the cart 10 may be removed from the platform (FIG. 8).

A dumping cart 57 is placed directly in front of the lift 43 and the collection cart 10 is pulled from the platform into the dumping cart 57 through one of its open ends. A pair of cross bars 65 extend transversely between the top of sides 60 and 61 and are spaced apart a distance less than the length of the open top end 11 of the collection cart 10 to trap the open end of the cart 10 when the dumping cart 57 is inverted. The pivotal locking arms 66 at each of the open ends 63 and 64 are locked in a horizontal position to retain the cart 10 from moving outward through the open ends. The dumping cart 57 is transported to the general waste disposal area. The dumping cart 57 is provided with crossmembers 68 on one side which are adapted to receive the existing lifting members of an existing conventional dumping compactor device 75. The dumping compactor locks onto the dumping cart 57 containing the collection cart 10 and lifts it in an arc to dump the contents of the collection cart into the compactor. 75.

It should be understood that the above described method and apparatus is suited to interface with existing sterilization and disposal equipment and that the lift and the dumping cart may not be required in all systems. In some instances, the doorway of the autoclave may be disposed close enough to the floor to directly receive the collection cart, and in some installations the dumping compactor may be adapted to directly receive the collection cart after sterilization.

Although this invention has been described fully and completely with special emphasis upon a preferred embodiment, it should be understood that within the scope of the appended claims the invention may be practiced otherwise than as specifically described herein.

I claim:

1. A system of apparatus for handling biologically infectious solid and fluid waste materials to prevent contamination of handlers of such waste materials comprising;

a collection cart comprising side walls having a generally open-walled construction and means defining a first top opening for receiving bags of infectious waste material, a transport cart of enclosed construction for removably receiving, enclosing, and safely transporting said collection cart, while protecting the handler against contamination, said transport cart further including means defining a second top opening, said collection cart being removably receivable within said transport cart, with said first top opening and said second top opening being alligned so as to receive bags of infectious waste materials into said collection cart when said collection cart is located within said transport cart, and a steam autoclave comprising means defining a front-opening sterilizing chamber with an entrance for receiving said collection cart and the solid and fluid contents thereof and means for subjecting said collection cart and the contents thereof to steam heat sufficient to kill pathogenic organisms.

2. A system of apparatus according to claim 1 further including
a biological indicator probe containing a thermocouple for insertion into the contents of said collection cart to monitor the temperature thereof.

3. A system of apparatus according to claim 1 in which
said sterilizing chamber includes additional heating means for subjecting the bags of waste material in said collection cart to dry heat following said steam heat sterilization in order to heat the bags to a temperature and for a period of time sufficient to melt syringes and other plastic articles contained within the waste material.

4. A system of apparatus according to claim 1 in which
said steam heating means are operable to provide steam at a temperature of 250° to 280° F., and a pressure of 35 p.s.i.g.

5. A system of apparatus according to claim 1 including
bags for waste material which are constructed of low density polyethylene film which will partially melt at temperatures in excess of 180° F.

6. A system of apparatus according to claim 1 including
bags for waste material which are constructed of high density polyethylene film.

7. A system of apparatus according to claim 1 including
bags for waste material which are constructed of high density polypropylene film.

8. A system of apparatus according to claim 1 wherein said collection cart further includes
a disposable bottom insert member and a disposable lining on the interior of the side walls of said collection cart so as to facilitate air removal, steam circulation, and fluid drainage within said collection cart.

9. A system of apparatus according to claim 8 in which
said bottom insert member comprises a flat corrugated cardboard insert with means defining a plurality of longitudinal openings therethrough and means defining a plurality of notches at each end of said cardboard insert.

10. A system of apparatus according to claim 8 in which
said disposable lining comprises a heavy weight paper liner having open top and bottom ends and which is positioned against said side walls of said collection cart.

11. A system of apparatus according to claim 1 in which said second top opening comprises
an open top panel with a first door hinged thereon, and wherein said transport cart further comprises imperforate bottom, front, back, and side panels with said front panel having means defining an opening therein, with a second door hinged on said front panel, casters attached underneath said cart in a supporting relation thereto, and
handle means attached to at least one of said panels for moving said transport cart.

12. A system of apparatus according to claim 11 including
locks for each of said doors.

13. A system of apparatus according to claim 11 further including;
a lift apparatus positioned directly in front and below the entrance to said sterilizing chamber and at the same height as the bottom panel of said transport cart and comprising a vertically-adjustable platform member for receiving and lifting said transport cart to a height sufficient to be received within the entrance of said sterilizing chamber, and
means for moving said platform member between a lowered and raised position.

14. A system of apparatus according to claim 13 in which
said platform member has vertically extensible and retractable front stop means at a front end thereof wherein said front stop means extends vertically when said platform is in the lowered position to prevent forward movement of said transport cart and retracts when said platform is in the raised position to permit said cart to enter and be removed from said sterilizing chamber, and
vertically extensible and retractable rear stop means on a back end of said platform, wherein said rear stop means extends vertically when said platform is in the raised position to prevent backward movement of said transport cart and retracts when said platform is in the lowered position to permit said cart to be received thereon and to be removed therefrom.

15. A system of apparatus according to claim 1 further including
a dumping cart of a size and shape to removably receive, contain and transport said collection cart.

16. A system of apparatus according to claim 15 in which
said dumping cart further comprises;
an imperforate bottom panel,
two opposing perforate side panels each having a top and bottom portion, and means defining two opposing open ends to receive said collection cart,
a pair of cross bars extending parallel and transversely between the top of said side panels and separated by a distance less than the length of said collection cart to retain said collection cart when said dumping cart is inverted,
pivotal locking arms at each of said open ends adapted to lock in a horizontal position to retain a collection cart from moving outward through said open ends,
handle means located on at least one end of said dumping cart, and
casters attached underneath of said dumping cart.

17. A system of apparatus according to claim 15 in which
said dumping cart further includes a plurality of supporting members positioned to cooperate with conventional dumping and compacting apparatus for lifting said dumping cart to dump the contents from said collection cart for disposal.

18. A system of apparatus according to claim 17 in which
said dumping cart further comprises;
an imperforate bottom panel,
means defining two opposing open ends to receive said collection cart,
a pair of cross bars extending parallel and transversely between the top of said said panels and separated by a distance less than the length of said collection cart to retain said collection cart when said dumping cart is inverted, pivotal locking arms at each of said open ends adapted to lock in a horizontal position to retain said collection cart from moving outward through said open ends, handle means located on at least one end of said dumping cart, and casters on the bottom panel of said dumping cart.

19. A system of apparatus according to claim 1 in which said sterilizing chamber further comprises means defining a bottom with a first fluid receiving means and fluid drain means, and said collection cart further comprises a second fluid receiving means and drain valve means for the release of the fluid contents to the bottom of said sterilizing chamber, and said first fluid receiving means and said second fluid receiving means being cooperable to retain the fluid contents released during sterilization.

20. A system of apparatus according to claim 19 in which said entrance into said sterilizing chamber comprises means defining a front opening, said front opening having a bottom portion and a valve actuating means at the bottom portion which is cooperable with said drain valve means to open the same upon said collection cart entering said sterilizing chamber and to close said drain valve means as said cart is removed from said autoclave.

21. A system of apparatus according to claim 19 in which said side walls comprise three perforate side panels and one imperforate side panel, and said collection cart further comprises an imperforate bottom portion wherein said second fluid receiving means and said drain valve means are in fluid communication with said bottom portion for disposing of the fluid contents from the collected waste material, at least one pivotally mounted perforate panel member horizontally positioned a short distance above said bottom portion to facilitate air removal, steam circulation, and fluid drainage within said cart, casters attached to said bottom portion, and handle means attached to at least one side wall of said collection cart.

22. A system of apparatus according to claim 21 in which said second fluid receiving means comprises a first inclined drain pan, said first fluid receiving means comprises a second inclined drain pan in the bottom thereof which is inclined in a direction opposite to the incline of said first drain pan.

23. A system of apparatus according to claim 21 in which said entrance into said sterilizing chamber further comprises means defining a bottom portion and a valve actuating means at the bottom portion of the entrance cooperable with said drain valve means to open the same upon said collection cart entering said sterilizing chamber and to close said drain valve means as said cart is removed from said autoclave.

24. A system of apparatus according to claim 21 in which said collection cart further includes a plurality of supporting members positioned to cooperate with a conventional dumping and compacting apparatus for lifting said collection cart to dump the sterilized contents for disposal.

25. A system of apparatus for handling biologically infectious waste materials to prevent contamination of handlers of such waste materials comprising a front-opening steam autoclave with means defining a sterilizing chamber for subjecting the contents thereof to steam heat sufficient to kill pathogenic organisms and means defining a front opening for access into said sterilizing chamber, a collection cart comprising side walls having a generally open-walled construction and means defining a first top opening for receiving bags of infectious waste material, a transport cart of enclosed construction for removably receiving, enclosing, and safely transporting said collection cart while protecting the handler against contamination, said transport cart further including means defining a second top opening, said collection cart being removably receivable within said transport cart, with said first top opening and said second top opening being alligned so as to receive bags infectious waste materials into said collection cart when said collection cart is located within said transport cart, and said transport cart further comprising means defining a front opening and a first door sealing said front opening, wherein said front opening permits the transfer of said collection cart into the front opening of said sterilizing chamber.

26. A system of apparatus according to claim 25 in which said sterilizing chamber having means defining a bottom which includes a first fluid receiving means and fluid drain means, said collection cart further includes a second fluid receiving means and drain valve means for the release of the fluid contents to the bottom of said sterilizing chamber, and said second fluid receiving means and said sterilizing chamber being cooperable to retain the fluid contents released during sterilization whereupon the sterilized fluids exit through said drain means.

27. A system of apparatus according to claim 26 in which said side walls of said collection cart comprises;

three perforate side panels and one imperforate side panel, said collection cart further comprises an imperforate bottom portion wherein said second fluid receiving means and drain valve means are in fluid communication therewith for disposing of the fluid contents from the collected waste material, at least one pivotally mounted perforate panel member horizontally positioned a short distance above said bottom portion to facilitate air removal, steam circulation, and fluid drainage within said collection cart, casters attached to said bottom portion, and pg,31 handle means attached to at least one of said side wall of said collection cart.

28. A system of apparatus according to claim 27 in which said second fluid receiving means comprises a first inclined drain pan and said first fluid receiving means comprises a second inclined drain pan which is inclined in a direction opposite to the incline of said first drain pan.

29. A system of apparatus according to claim 27 in which said second top opening comprises;

an open top panel with a second hinged door thereon, wherein said transport cart further comprises imperforate bottom, front, back, and side panels, casters attached on the bottom panel in supporting relation thereto, and handle means attached to at least one of said panels for moving said transport cart.

* * * * *